United States Patent [19]

Visentin et al.

[11] Patent Number: 4,734,187
[45] Date of Patent: Mar. 29, 1988

[54] CONSTANT SUCTION GRADIENT PUMP FOR HIGH PERFORMANCE LIQUID CHROMATOGRAPHY

[76] Inventors: William Visentin, 11910 Butternut St., Palm Beach Gardens, 33410; William T. Casey, Jr., 1370 Birkdale Dr., West Palm Beach, both of Fla. 33414

[21] Appl. No.: 874,189

[22] Filed: Jun. 13, 1986

[51] Int. Cl.[4] .............................................. B01D 15/08
[52] U.S. Cl. ................................. 210/101; 210/198.2; 417/521
[58] Field of Search ..................... 210/656, 101, 198.2; 417/521

[56] References Cited

U.S. PATENT DOCUMENTS

| | | | |
|---|---|---|---|
| 3,816,029 | 6/1974 | Bowen | 417/539 |
| 3,981,620 | 9/1976 | Abrahams | 417/42 |
| 4,045,343 | 8/1977 | Achener | 210/101 |
| 4,137,011 | 1/1979 | Rock | 417/42 |
| 4,155,683 | 5/1979 | Mochizuki | 417/269 |
| 4,173,437 | 11/1979 | Leka | 417/521 |
| 4,245,963 | 1/1981 | Hutchins | 417/540 |
| 4,264,287 | 4/1981 | Ishida | 417/540 |
| 4,448,692 | 5/1984 | Nakamoto | 210/101 |
| 4,566,858 | 1/1986 | Akiba | 417/45 |

OTHER PUBLICATIONS

"Varien 'Slim-Line' Series 2000 Liquid Chromatography components", undated, p. 3.

Primary Examiner—Ernest G. Therkorn
Attorney, Agent, or Firm—Woodcock, Washburn, Kurtz, Mackiewicz & Norris

[57] ABSTRACT

A gradient cam is used in an HPLC pump for controlling proportions of HPLC solvents on the low pressure side of the pump. The gradient cam is not concentric, and has an upward or draw slope along 190° of its circumference and a downward or thrust slope along 170° of its circumference. In operation, the cam is designed to be used with two followers, located 180° apart, which follow along the cam's gradient. The unique cut of the cam insures a constant suction on the inlet or suction side of the cam during the entire pump cycle. During the 20° period of the cycle in which both followers are simultaneously on the 190° suction ridge, the slope of that portion of the gradient is one half of that of the remaining portion of the 190° portion. The gradient cam provides both linear draw and output pressure.

19 Claims, 6 Drawing Figures

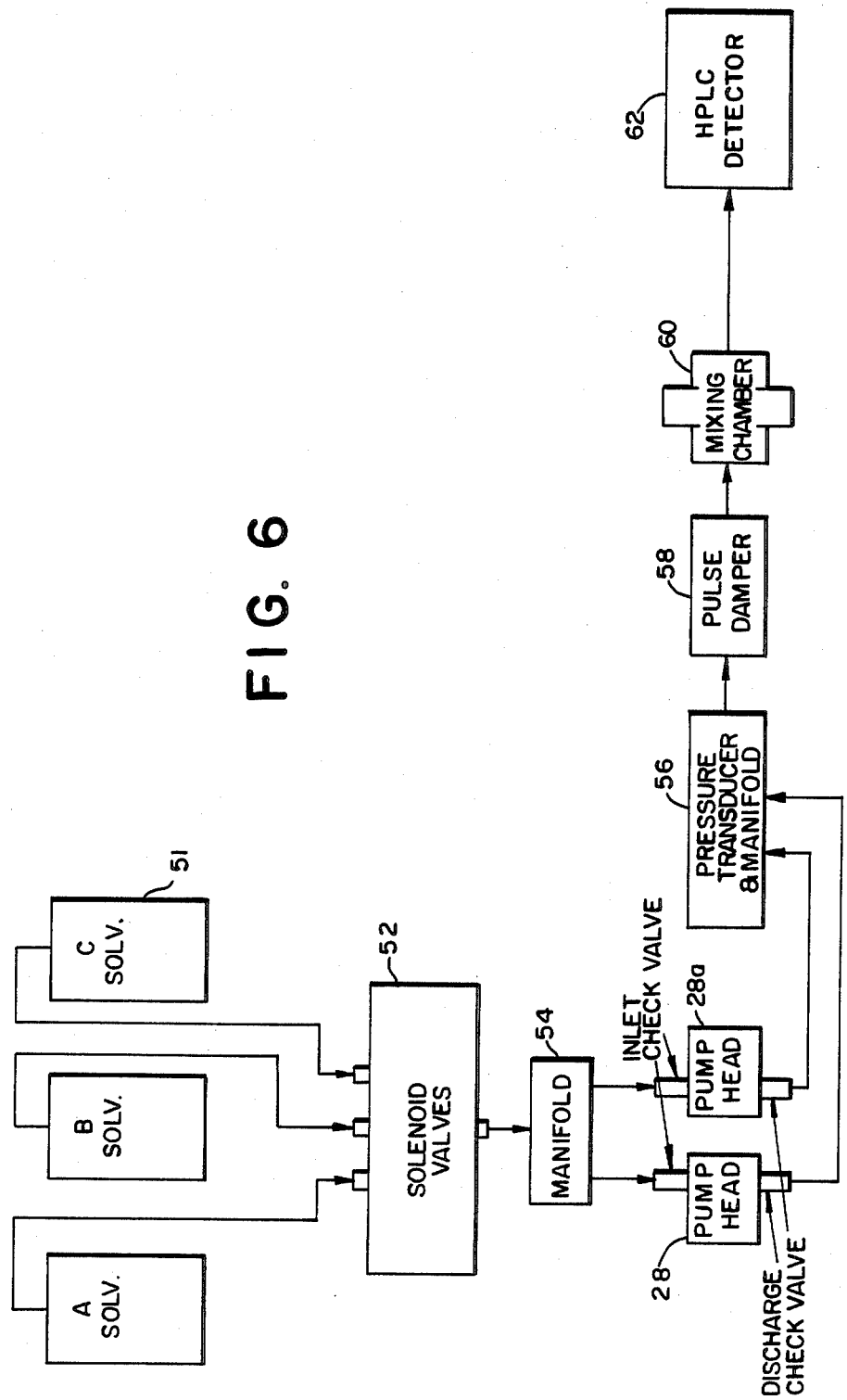

CONSTANT SUCTION GRADIENT PUMP FOR HIGH PERFORMANCE LIQUID CHROMATOGRAPHY

BACKGROUND OF THE INVENTION

This invention relates generally to liquid chromatography, and more specifically to a solvent supply system for use in high performance column liquid chromatography (HPLC), in which the control of the proportioning of solvents on the low pressure or inlet side of the pump is by means of a specially designed gradient suction cam.

Chromatography is a separation method in which a mixture of components (called the "sample" or "sample mixture") is placed as a zone at one end of a system containing both a stationary phase and a mobile phase. Each component of the sample distributes itself in dynamic equilibrium between the two phases in a ratio characteristic of that component. As a result, the flowing mobile phase causes each individual component zone to migrate at a characteristic rate, and the zones become separated after a period of time. In liquid absorption chromatography, the stationary phase consists of a tubular column packed with an absorbent material. The mobile phase for carrying an analysis sample through the column commonly referred to as the carrier, is a solvent mixture comprising two or more miscible liquids, which are introduced into the column. An equilibrium is established for the individual components of a sample mixture according to the "attraction" of each to the stationary phase and according to the solubility of each in the carrier solvent. The rate at which a solute passes through the column chromatograph is dependent upon the existing equilibrium points. Separations occur where the distributions differ.

All liquid chromatography systems include a moving solvent, a means for producing solvent motion such as gravity or a pump, a means for sample introduction, and a fractionating column. Operation of a liquid chromatography system with a carrier of two or more solvents mixed in constant, nonvarying proportions is referred to as isocratic operation.

It is often desirable to operate the liquid chromatographic system using a carrier in which the ratios of the liquid in the solvent mixture vary over time in accordance with some predetermined gradient. This type of operation is referred to as gradient elution, and the gradient profiles referred to as solvent programs. Within the category of gradient elution operation, the ratios in the solvent mixture can be made to increase at a fixed rate, i.e. linear gradient or at an increasing rate of change, i.e., convex gradient or at a decreasing rate of change, concave gradient by appropriate control of the solvent mixing apparatus.

There are various types of chromatography, e.g., liquid chromatography, gas chromatography, thin layer chromatography, etc. The major differences between these various chromatographic methods lie in the physical state of the mobile phase (gas or liquid), and the manner in which the stationary phase is supported, e.g., coated on an inert granular material packed in a tube, coated on an inner wall surface, etc. In all chromatographic methods, the separation objective is essentially the same, that is, distribution of the sample components between a mobile phase and a stationary phase. When the method is used for chemical analysis, a detector is commonly placed at the far end of the system to monitor the passage of the component zones as they emerge from the system. The signal from the detector is displayed on a recording device such as a strip chart recorder, and a record indicates both qualitative and quantitative information regarding the components of the sample.

It is often desirable for a chromatographic system to be able to provide high resolution (i.e., a large degree of component separation with narrow zones), evenly spaced component zones, rapid separation, and a satisfactory record from a very small sample. The behavior of the system described in these terms may be called the "performance" of the system. It is well known in the chromatographic art to improve system performance by changing one of the system variables during the course of the analysis such as temperature, chemical composition of the mobile phase, and the flow rate of the mobile phase.

An essential objective relevant to all liquid chromatography apparatus of the type considered herein, is that of providing a proper flow of solvent to and through the chromatographic column. Thus, in the past, numerous and varied approaches have been utilized for supplying solvents to high performance liquid chromatographic columns.

A key requirement in this regard is that of providing a relatively nonpulsating, constant flow of solvent. In addition, because an LC (liquid chromatography) detector is sensitive to flow rate variations, it can provide erroneous readings and exhibit excessive noise in the presence of a pulsating solvent flow. Various approaches have been utilized in the past in order to remove pulsation and other noise. In general, however, the prior art methodology was directed toward highly expensive and overly complex mechanisms for controlling pulsation. Thus, in a typical example in which a system is intended for operation in a gradient elution mode, i.e., by use of two distinct solvents, a dual cylinder pump arrangement has been utilized. Such an arrangement requires distinct cylinder pumps, including separate means for driving each of the pumps, thereby requiring separate speeds, etc.

A liquid chromatography system which utilizes a solvent pump, can control the pulsating problem by applying control means at either the low pressure or the high pressure end of the pumping stage. The low pressure end of the pumping system is the inlet or suction side of the pump. The high pressure end of the pumping means is the pumping side of the pump mechanism. The overwhelming majority of systems in the prior art are directed toward controlling pump pulsation on the high pressure end of the system.

Pulsation control has typically been provided by a complex mechanical means on the high pressure end of the system or through an electronically actuated feedback circuit which would control motor speed, or another flow parameter. Thus, in U.S. Pat. No. 4,045,343 entitled "High Pressure liquid Chromatography System", pulsation control was provided through means of a complex system of valves and control apparatus. In U.S. Pat. No. 3,985,021 entitled "High Performance Liquid Chromatography System", feedback means were provided for controlling the rotational speed of the motor throughout the reciprocating cycle of the pump so as to provide the preselected rotational speeds over predetermined subintervals of each successive reciprocation cycle. Application of the control cycle was synchronized with the pumping cycle so that the speed control was properly applied over each successive reciprocating cycle in order to control output pulsation. In U.S. Pat. No. 3,981,620 entitled "Pumping Apparatus", control on the high pressure side of the pumping mechanism was also achieved through a pressure sensing device which incorporated a feedback system to control the speed of the motor. This feedback system not only controlled the speed of the motor but provided a means to limit the current to the motor such that only the current necessary to drive the pump was provided. U.S. Pat. No. 4,245,963, entitled "Pump", disclosed a method for controlling pulsation of the output or high pressure side of the pump by means of a liquid storage device consisting of a flattened length of coiled tubing which was placed in the flow path between the two chambers to deliver flow during the low periods when the displacement elements were in reverse direction, thereby smoothing flow delivery. Finally, U.S. Pat. No. 3,981,620 also entitled "Pumping Apparatus", utilized a feedback responsive mechanism to sense the pressure of the liquid being pumped. It utilized a "flow through" meter which comprises a conduit as its pressure sensitive element.

Several prior art systems utilized mechanical analog systems incorporating specialized cam technology for control on the high pressure side of the pump. U.S. Pat. No. 4,137,011, entitled "Flow Control System For Liquid Chromatographs," provides a control system which was particularly adapted to use in multiple chamber single pump systems in which a cam driven by a speed control device such as a stepping motor is connected to a multiple chamber positive displacement piston pump arranged with its chambers and associated pumps in opposition to either other on each side of the cam. The invention also utilizes a complex feedback network which controls the speed of the pump.

The model 2010 HPLC isocratic pump by Varian Associates is an example of a current system on the market which utilizes both cam technology and an electronic feedback mechanism to control pulsation on the high pressure side of the pumping cycle. This system utilizes a concentric face cam to facilite suction and pulsation, and also incorporates a pressure feedback system for solvent compressability compensation. The system utilizes a pressure transducer which provides high resolution for accurate readout of system operating pressure. The pressure feedback system controls motor speed, based upon the actual operating backpressure, to compensate for solvent compression and minimize pump pulsation.

While the majority of prior art systems sought to control the high pressure side of the pumping cycle, there are major advantages to be realized by the control of the low pressure or inlet side of the pump. This is particularly true where the examination of multiple solvents is desired, and there is a need to proportion the solvents evenly. In such cases, it is desirable to provide an even and nonpulsating flow of solvents from the solvent reservoirs to the pump head. The prior art systems which sought to control the high pressure side of the pumping process create a rapid unequal draw on the low pressure or inlet side of the pump. This makes the proper proportioning of multiple solvents difficult, and requires the use of expensive specialized check valves and electronic sensing means. Moreover, with the improvement in downstream pulse dampening technology, it is no longer as necessary to control pulsation through the pumping means on the high pressure side.

One system currently on the market for controlling the low pressure side of an HPLC pump is manufactured by IBM. It utilizes a cam system with three pumping cross head followers, spaced at 120° intervals about the cam. While the IBM system provides constant suction on the low pressure or inlet side of the pump, it does so at the considerable expense of an additional cross-head follower, pumping head and check valve configuration. This of course, adds extra expense and complication to the pumping procedure. The pumping barrel and check valves are the most expensive parts of an HPLC pumping system.

It would be desirable to control the flow of HPLC solvent on the low pressure or inlet side of the pump by means of a two follower cross-head pumping mechanism which could provide constant suction on the inlet side of the pump by means of a specially shaped gradient cam. This would be particularly desirable in applications in which there is a need for constant suction to proportion various solvent samples. By providing constant and uniform suction, the user could get an even proportioning of solvent. Such a system would provide the user with the ability to obtain a very smooth draw of solvent on the inlet or low pressure side of the pump.

It is the purpose of the disclosed constant suction proportioning pump to provide a constant and uniform draw of solvent on the low pressure side by means of a specially shaped gradient face cam. It is a second purpose of the disclosed proportioning pump to provide a constant suction by a relatively simple and inexpensive means on the inlet side using only two cross-head followers spaced 180° apart. The gradient cam of the disclosed preferred embodiment is divided unevenly by a peak and trough extending radially from the center of the cam. 170° of the cam profile is used to force the piston forward and therefore pump solvent. 190° of the cam profile is used to draw a constant flow of solvent on the low pressure side of the pump. Because over one half of the surface of the cam gradient is devoted toward the draw side of the pump, and the followers are spaced evenly at 180° intervals, the cam provides continuous suction. The system requires no complicated software and controls any pulsation on the high pressure side with improved pulse dampening mechanisms downstream from the pumping means. The pumping means accordingly receives a steady, properly proportioned flow of solvent.

SUMMARY OF THE INVENTION

In accordance with the invention, a cam provides a constant suction on the low pressure or inlet side of an HPLC pumping system. The cam is disk-shaped, with a gradient profile specifically cut to provide a constant and uniform suction when used with two roller followers, spaced 180° apart, which ride along the cam's profile. The gradient cam includes a central orifice and a groove which couples with the electromechanical drive.

The profile of the cam is divided into two unequal sections by a peak and trough running radially from the center of the cam. The peak represents the greatest point of profile ridge protrusion and the trough represents the lowest point of profile ridge protrusion.

The disk-shaped cam is divided by the peak and trough into a first ridge section comprising 170° of the total circumference of the cam and a second ridge section comprising the remaining 190° of the gradient cam's circumference.

When the cam is rotated in a counterclockwise direction with respect to its face, the gradient profile ridge rises over the 170° portion of the ridge and declines over the 190° portion of the ridge. When in operation, the rising of the ridge corresponds with the pumping portion of the pump cycle, and the decline of the ridge corresponds with suction. Because the followers are held stationary and located 180° apart, and the suction gradient corresponds with 190° of the cycle, the pump continuously provides suction. In order to compensate for the 20° of the cycle in which both followers are on the 190° portion of the profile ridge, the gradient of the cam is reduced by one-half over that portion of the pump cycle.

BRIEF DESCRIPTION OF THE DRAWINGS

FIG. 6 is a flow chart diagram of a HPLC pumping system which utilizes the proportioning pump of the preferred embodiment.

DESCRIPTION OF THE PREFERRED EMBODIMENT

The preferred embodiment is described with reference to the above enclosed drawings wherein the same numbers are used.

Figure 1:
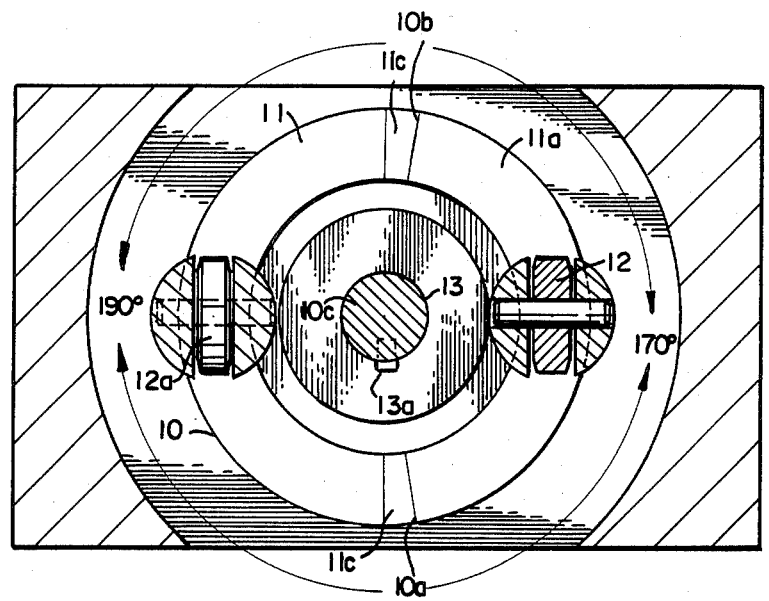
FIG. 1 is an elevated view of the preferred gradient cam embodiment.

Referring to FIG. 1, an elevated view of the preferred gradient cam and cross-head followers is shown. The gradient cam 10 of the preferred embodiment is a circular disk shaped face cam which in operation rotates in a counterclockwise direction with respect to its face. The gradient cam 10 has a profile ridge 11 along the circumference of the disk on which two stationary cross-head assemblies and roller followers 12, 12a, spaced 180° apart, ride. The profile ridge 11 of gradient cam 10 is divided into two unequal sections by a peak 10a and a trough 10b extending radially from center 10c of the gradient cam. Peak 10a represents the point of greatest profile protrusion, and trough 10b represents the point of least profile protrusion.

Gradient cam 10 also has a central orifice 13 and groove 13a designed to couple with and hold a drive shaft driven by electromechanical operating means, thereby enabling the counterclockwise revolution of the gradient cam 10. Peak 10a, and trough 10b divide ridge 11 of gradient cam 10 into a first profile ridge section 11a comprising 170° of the circumference of the entire profile ridge 11 and a second profile ridge section 11b comprising 190° of the circumference of the entire profile ridge 11.

Because the gradient cam of the preferred embodiment rotates in a counterclockwise direction, the profile ridge section 11a rises with respect to the cam face over 170° of the rotation and profile ridge section 11b declines over 190° of the cam rotation period. The angular distance along profile ridge section 11a is therefore 20° less than that of profile ridge section 11b. As can be seen from shading 11c, because the followers are 180° apart there is a 20° portion of profile ridge section 11b adjacent to the peak 10a and trough 10b in which both followers ride simultaneously. In operation in the preferred embodiment, profile ridge section 11a causes the downward thrust of the pumping portion of the cycle, and profile ridge section 11b causes the longer suction or inlet portion of the pumping assembly.

Figure 2:
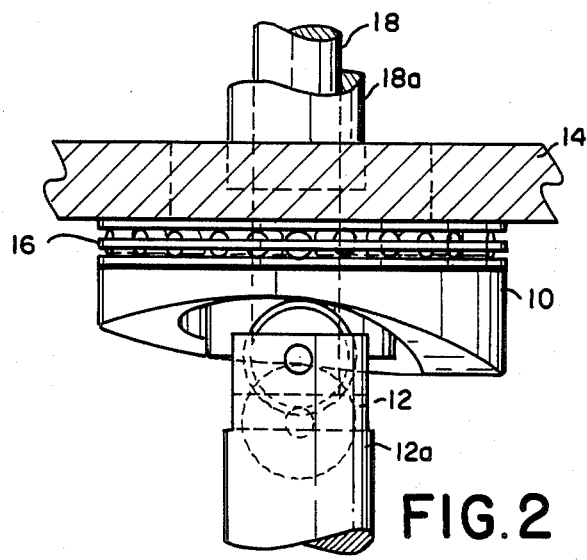
FIG. 2 is a side view of the preferred cam embodiment illustrating cross-head assemblies and roller followers attached thereto.

Referring to FIG. 2, a side view of the gradient cam of the preferred embodiment is illustrated. As shown, in operation, the face of the gradient cam extends downward. The gradient cam 10 is attached to the pump housing 14 and rotates with the aid of roller bearings 16. Also illustrated are the drive shaft 18 and clutch assembly 18a which are attached to the orifice 13 and groove 13a of the gradient cam 10 through its rear, and which when attached to electromechanical drive means, rotate gradient cam in a counterclockwise direction with respect to its face. Stationary cross head assemblies and roller followers 12, 12a separated by 180° are also shown riding along the profile ridge. Referring to the motion of the cross-head assemblies and followers 12, 12a, as gradient cam 10 rotates in a counterclockwise direction, with respect to the cam's face, cross-head assemblies and rollers followers 12, 12a are alternatingly thrusted downward and upward along the profile ridge 11 of gradient cam 10. Accordingly, because over half the profile ridge represents the suction portion of the pumping cycle, and because cross-head assemblies and roller followers 12, 12a are spaced evenly 180° apart on profile ridge 11, the pump provides continuous suction.

Figure 3:
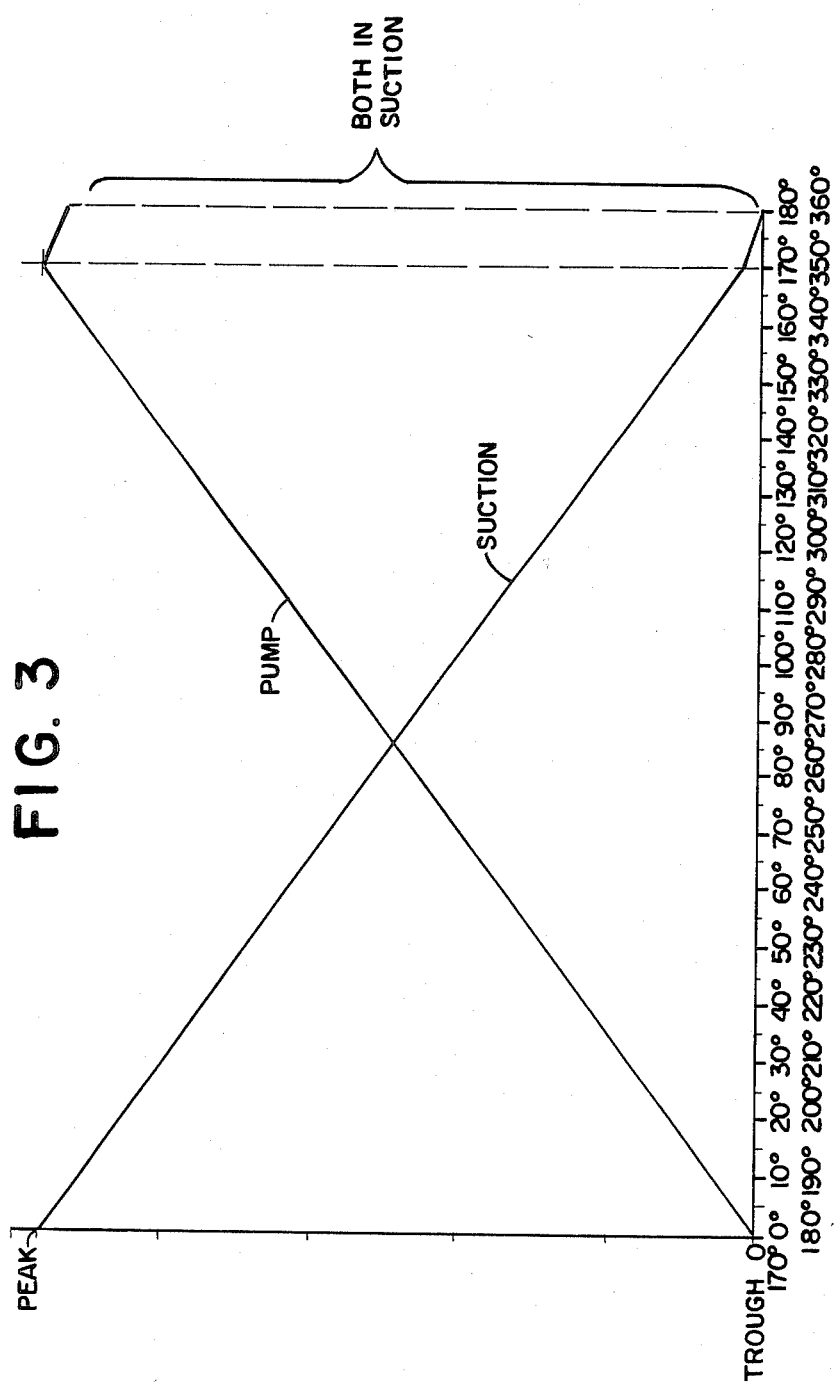
FIG. 3 is a graphical illustration of the draw and pulse characteristics of the gradient cam.

The operation of the gradient cam of the preferred embodiment is more clearly illustrated by the the graphical flow chart of FIG. 3. Graphical representations of the movement of the cross head assemblies and roller followers are shown 180° out of phase with each other. Both the suction or inlet and high pressure action of the cam are linear. Thus, profile ridge 11 of gradient cam 10 is cut uniformly and linearly on both sides of peak 10a and trough 10b. FIG. 3 illustrates the simultaneous movement of the followers. As can be seen a follower draws on the inlet side for 170° of the 360° of the pump cycle, and pulses during the 0° to 170° period of the cycle. During the 20° interval in which both cross head assemblies and roller followers are simultaneously on profile ridge section 11b, the slope (gradient) of the ridge is one-half of that when only one follower is in the suction mode. This occurs when the followers are simultaneously at the 170° to 180° phase point and at the 350° to 360° phase point, respectively. Thus, as illustrated graphically, at all times, there is a constant and uniform suction on the inlet side of the pump.

While numerous variations in cam geometry are possible, the gradient cam on which FIG. 3 was based resulted in a gradient rise and decline of 0.003 inches on both the inlet and high pressure sides for each degree of cam rotation During the 20° of rotation in which both followers are in the suction mode, the gradient was cut at 0.0015 of an inch. Thus at all times there was a uniform and linear suction on the inlet side of the pump.

Figure 4:
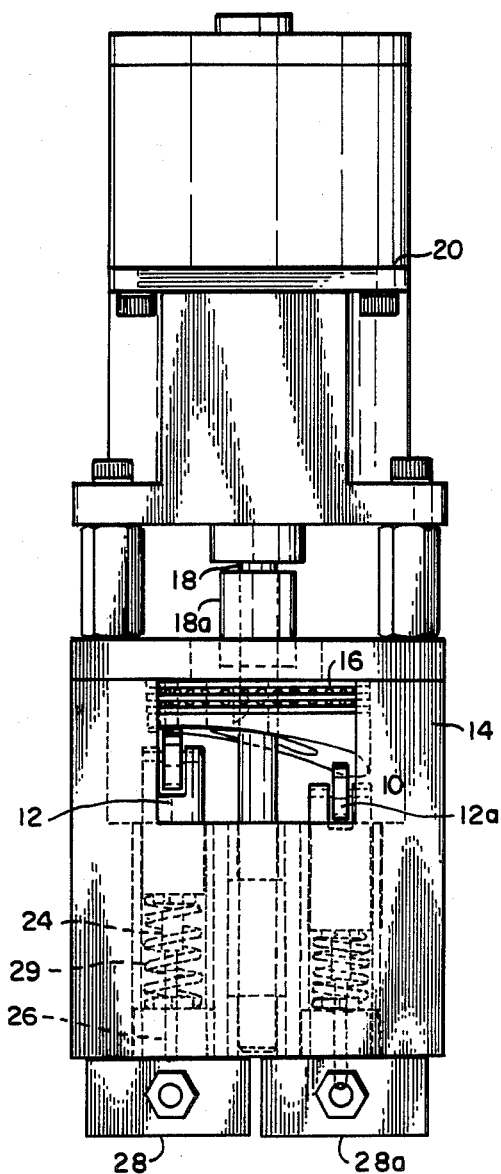
FIG. 4 is a side perspective view of the entire pumping mechanism of the preferred embodiment.

Referring to FIG. 4 a side view of the complete pumping mechanism and constant suction gradient cam of the preferred embodiment are shown. As illustrated, the preferred embodiment contains a pump housing 14 which houses the gradient cam 10. Gradient cam 10 is situated within the cam housing and rotates with the aid of roller bearings 16. Electromechanical driving means 20 of a conventional type can be used to turn the cam. The electromechanical driving means 20 of the preferred embodiment should be able to rotate the gradient cam at approximately 50 rpm in a counterclockwise direction with respect to the face of the gradient cam. Accordingly, in operation the gradient cam 10 should complete a revolution every 1.20 seconds.

The gradient cam 10 is directly driven by a drive shaft 18 attached to a slipper clutch 18a which attaches to the rear of gradient cam 10 through its central orifice 13. Referring to the lower portion of FIG. 4, the two stationary cross-head assemblies with respective roller followers 12, 12a are illustrated. FIG. 4 also illustrates that attached to each cross head assembly and follower 12, 12a are plunger assemblies 24 with sapphire pistons 26 which are injected into respective pumping heads 28, 28a. Each of the two cross head assemblies and followers 12, 12a, plunger assemblies 24 and sapphire pistons 26 has a spring 28 which keeps each respective cross head and follower 12, 12a on the profile ridge of the cam.

Figure 5:
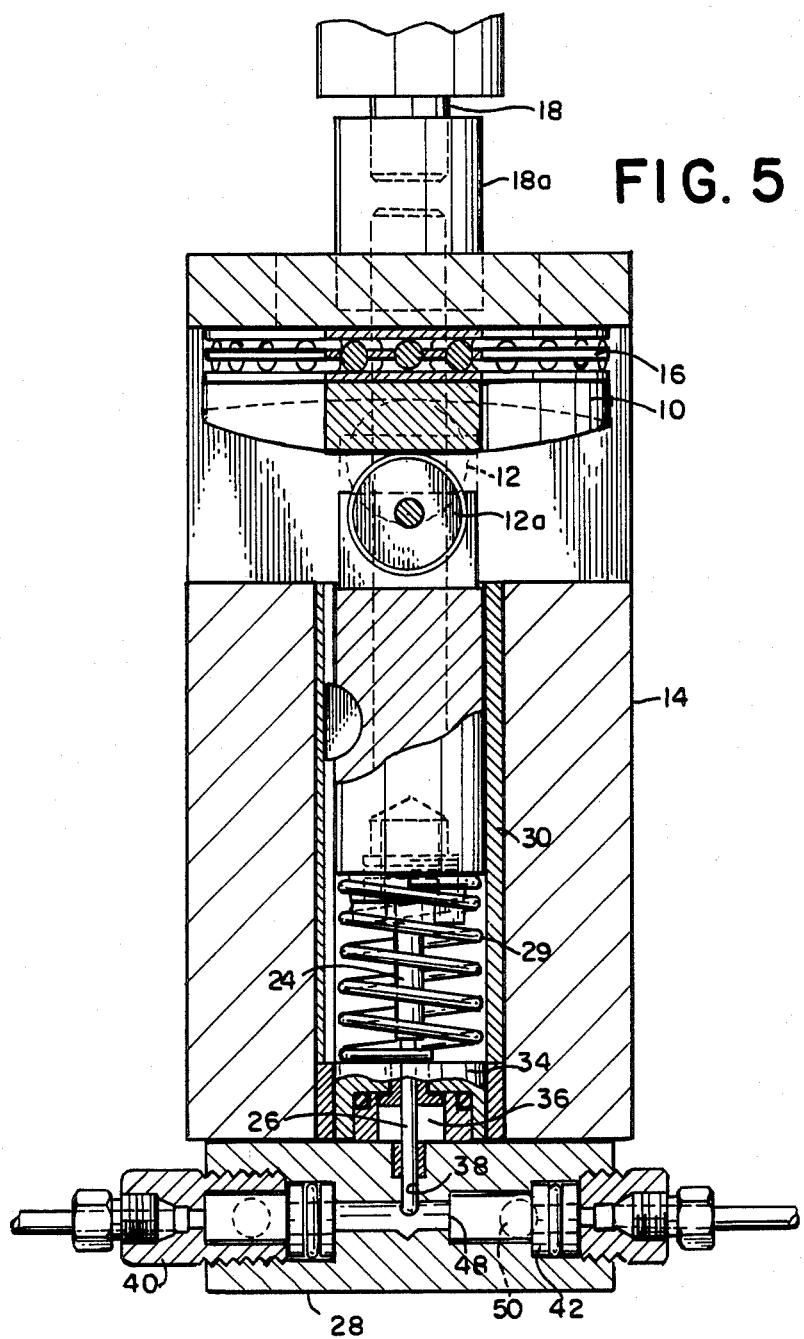
FIG. 5 is an enhanced view of the gradient cam, cross-head assembly, pump assembly and pump head.

Referring to FIG. 5, an enhanced side view of the lower portion of the entire cam drive mechanism is illustrated. As illustrated gradient cam 10 is situated within the pump housing and rotates with the aid of roller bearings 16. Also illustrated is a side view of the one stationary cross head assemblies and roller followers 12, 12a. The entire cross head assemblies fit within a hollow cylindrical chamber 30 located within the pump housing 14. As can be seen, each cross head assembly and roller follower 12, 12a are kept on the face cam by means of a spring 28 situated at the lower most proximity of the hollow cylindrical chamber 30. The spring 28 is held in place by a circlip 32 and cylindrical support 34. At the lower most portion of the cross head assembly is the plunger assembly 24 and sapphire piston 26. The plunger assembly 24 has an attachment 35 which mates with the bottom of each cross head assembly and follower 12.

In operation as gradient cam 10 rotates, the crosshead assemblies and followers 12, 12a ride the gradient cam along ridge 11 and alternatively are thrust downward by the gradient cam. Each plunger assembly 24 and sapphire piston 26 is accordingly alternatingly thrust downward and upward into the pumping head through a cylindrical seal 36 and cylindrical passage 38. Each pumping head 28, 28a comprises an inlet check valve 40 and outlet check valve 42, a passage for the flow of solvent 44 between the inlet and outlet check valves, and a pumping chamber 46.

Each check valve assembly of the preferred embodiment comprises of a hollow sapphire seat 48 and a ruby ball 50 which acts alternatingly to permit and impede the flow of solvent. The check valve assembly of the preferred embodiment should be able to withstand internal pressure of 10 thousand lbs. per square inch.

Referring to FIG. 6, a flow chart diagram of an entire HPLC system utilizing the proportioning pump of the preferred embodiment is shown. As shown, the system of the preferred embodiment is capable of testing several sample solvents simultaneously. Each of the respective solvents is attached to a tri-head solenoid valve system 52 which permits the flow of each respective solvent over an equivalent portion of the flow cycle. Because of the constant suction created by the gradient cam of the preferred embodiment, proportioning by the solenoid is facilitated. Thus, the solenoid can be controlled by relatively simple timing software.

From the solenoid valve, each respective solvent goes through a manifold 54 which channels the solvent, and then into the inlet check valve of each respective pump head 28, 28a. The pump head then pumps the respective solvent out of the constant suction proportioning pump into a pressure transducer and manifold 56. Consequently, pulse dampening means 58 are used to remove any ripples or pulsations in the flow of the solvent. The solvent is then put into a mixing chamber 60 and then sent on to the HPLC detector 62.

While one embodiment is illustrated in the disclosure, it will be recognized by those skilled in the art that other embodiments fall within the spirit and scope of the claims contained herein. In particular it will be readily understood by those skilled in the art that the operation of the gradient cam, as diagramed in FIG. 3 could easily be replaced by any type of cam configuration which would achieve this flow characteristic.

What is claimed is:

1. In a HPLC system, a constant suction pump comprising:
   a rotatable, disk-shaped cam having a radient profile;
   two stationary roller followers spaced approximately 180° part, said roller followers riding along said gradient profile of said cam as it rotates;
   electromechanical driving means for rotating said cam; and
   two piston plungers attached to said roller followers, said piston plungers alternately pumping and drawing solvent;
   said gradient profile of said cam being divided into first and second profile sections, said first profile section having a constant gradient and said second profile section having a variable gradient, said second profile section being divided into first, second and third portions, said first and second portions each having a gradient approximately one-half of the gradient of said third portion; said third portion being located between said first and second portions;
   said piston plungers compressing when said rollerfollowers ride said first profile section when said cam is rotated in a first direction and
   said piston plungers expanding when said roller-followers ride over said second profile section when said cam is rotated in said first direction.

2. The constant suction pump recited in claim 1 wherein said electromechanical drawing means comprises a drive shaft and clutch means for rotating said cam.

3. The constant suction pump recited in claim 2 wherein said cam further comprises a central orifice having a groove for coupling with said drive shaft and clutch means.

4. The constant suction pump recited in claim 1 wherein said first profile section comprises less than half of total circumference of the gradient profile and the second profile section comprises over half of total circumference of the gradient profile.

5. The constant suction pump recited in claim 4 wherein each of said first and second portions of said second profile section comprises one half of total circumference that said second profile section exceeds said first profile section.

6. The constant suction pump recited in claim 5 wherein said first profile section comprises approximately 170° of total circumference of said gradient profile and said second profile section comprises approximately 190° of total circumference of said gradient profile.

7. The constant suction pump as recited in claim 6 wherein each of said first and second portions of said second profile section comprises approximately 10 ° of total circumference of gradient profile.

8. The constant suction pump as recited in claim 7 wherein the gradient of the first profile section and the third portion of said second profile section is approximately 0.003 of an inch per each degree of circumference and the gradient of the first and second portions of said second profile section are approximately 0.0015 of an inch per each degree of circumference.

9. The constant suction pump as recited in claim 1 wherein the gradient of the first profile section and the third portion of said second profile section is approximately 0.003 of an inch per each degree of circumference and the gradient of the first and second portions of said second profile section is approximately 0.0015 of an inch per each degree of circumference.

10. The constant suction pump as recited in claim 1 wherein said first profile section comprises approximately 170° of total circumference of said gradient profile and said second profile section comprises approximately 190° of total circumference of said gradient profile.

11. The constant suction pump as recited in claim 10 wherein each of said first and second portions of said second profile section comprises approximately 10° of total circumference of gradient profile.

12. The constant suction pump as recited in claim 11 wherein the gradient of the first profile section and the third portion of said second profile section is approximately 0.003 of an inch per each degree of circumference and the gradient of the first and second portions of said second profile section are approximately 0.0015 of an inch per each degree of circumference.

13. An HPLC proportioning solvent pump which provides constant inlet suction comprising:
   a pump housing for encasing said proportioning solvent pump;
   a rotatable, disk-shaped cam having a gradient profile along its outer periphery;
   two stationary cross-head assemblies and followers spaced approximately 180° apart, said cross-head assemblies and followers riding said gradient profile of said cam;
   means for keeping said cross-head assemblies and followers on said profile of said cam;
   two piston plungers attached to said cross-head assemblies and followers, said piston plungers alternately drawing and pumping solvent;
   electromechanical means for rotating said cam in a first direction; and
   a pumping head for each said piston plunger, each said pumping head comprising dual check valve assemblies for controlling pumping and drawing of solvent, a passageway between said dual check valves and a pumping chamber;
   said gradient profile of said cam being divided into first and second profile sections by a peak and a trough, said peak and trough extending radially from a center of the cam, said peak representing the greatest point of said gradient profile protrusion and said trough representing the lowest point of said gradient profile protrusion, said first profile section having a constant gradient and said second profile section having a variable gradient, said second profile section being divided into first, second and third portions, said first and second portions each having a gradient approximately one-half of the gradient of said third portion, said first portion being adjacent said peak and said second portion being adjacent said trough;
   said piston plungers compressing when said followers ride over said first profile section when said cam is rotated in a first direction;
   said piston plungers expanding when said followers ride over said second profile section when said cam is rotated in said first direction; and
   said first profile section comprises approximately 170° of total circumference of said gradient profile, said first and second portions of said second profile section each comprises approximately 10° of total circumference of said gradient profile and said third portion of said second profile section comprises approximately 170° of total circumference of said gradient profile.

14. The constant suction pump as recited in claim 13 wherein the gradient of the first profile section and the third portion of said second profile section is approximately 0.003 of an inch per each degree of circumference and the gradient of the first and second portions of said second profile section are approximately 0.0015 of an inch per each degeree of circumference.

15. In a HPLC system of the type having a HPLC detector, a constant suction pump comprising:
   a plurality of sources of solvent;
   a plurality of valves, one for each of said sources of solvent, said valves controlling the flow of solvent from said sources;
   a pump having an inlet side connected to draw solvent from said sources through said valves and an outlet side through which the solvents flow to said HPLC detector;
   electromechanical means for driving said pump; and
   means for providing constant suction on the inlet side of said pump, said constant suction means comprising:
   first and second plunger assemblies, each said plunger assembly displaceable for alternately drawing and pumping solvent; and
   means for compensating the displacement of said plunger assemblies when said first and second plunger assemblies simultaneously draw solvent, thereby providing constant suction, said compensating means further comprising:
   a rotatable, disk-shaped cam having a gradient profile divided into first and second profile sections, said first profile section having a constant gradient and said second profile section having a variable gradient, said second profile section being divided into first, second and third portions and said first and second portions having a gradient approximately one-half of the gradient of said third portion, said third portions located between said first and second portions;
   wherein said first and second plunger assemblies ride the profile of said cam, said first and second plunger assemblies each pumping solvent when riding said first profile section and drawing solvent at a first rate when riding the third portion of said second profile section and drawing solvent at a second rate when riding the first and second portion of said second profile section.

16. Apparatus of claim 15 wherein said first and second plunger assemblies are spaced approximately 180° apart.

17. Apparatus of claim 16 wherein said first profile section comprises approximately 170° of total circumference of said gradient profile and said second profile section comprises approximately 190° of total circumference of said gradient profile.

18. Apparatus of claim 17 wherein each of said first and second portions of said second profile section comprises approximately 10° of total circumference of said gradient profile.

19. Apparatus of claim 18 wherein the gradient of the first profile section and the third portion of said second profile section is approximately 0.003 of an inch per each degree of circumference and the gradient of the first and second portions of said second profile section are approximately 0.0015 of an inch per each degree of circumference.

* * * * *